US008765204B2

(12) United States Patent
Gassenmeier

(10) Patent No.: US 8,765,204 B2
(45) Date of Patent: Jul. 1, 2014

(54) CARBONOTHIOATES AS FLAVOURS AND FRAGRANCES

(75) Inventor: Klaus Gassenmeier, Volketswil (CH)

(73) Assignee: Givaudan S.A., Vernier (CH)

( * ) Notice: Subject to any disclaimer, the term of this patent is extended or adjusted under 35 U.S.C. 154(b) by 318 days.

(21) Appl. No.: 13/262,267

(22) PCT Filed: Apr. 7, 2010

(86) PCT No.: PCT/EP2010/054582
§ 371 (c)(1),
(2), (4) Date: Nov. 1, 2011

(87) PCT Pub. No.: WO2010/115920
PCT Pub. Date: Oct. 14, 2010

(65) Prior Publication Data
US 2012/0052178 A1    Mar. 1, 2012

(30) Foreign Application Priority Data
Apr. 7, 2009  (GB) .................................. 0906009.6

(51) Int. Cl.
*A23L 1/22*    (2006.01)
(52) U.S. Cl.
USPC .......................... 426/535; 426/534; 426/650
(58) Field of Classification Search
USPC ......................................... 426/534, 535, 650
See application file for complete search history.

(56) References Cited

U.S. PATENT DOCUMENTS

| | | | |
|---|---|---|---|
| 3,885,051 A | 5/1975 | Mussinan et al. |
| 3,978,240 A | 8/1976 | Van der Heijden et al. |
| 6,129,941 A | 10/2000 | Escher et al. |
| 7,585,535 B2 | 9/2009 | Grab et al. |
| 2004/0253362 A1 | 12/2004 | Grab et al. |
| 2008/0260670 A1 | 10/2008 | Natsch et al. |

FOREIGN PATENT DOCUMENTS

| | | |
|---|---|---|
| EP | 1 170 295 A1 | 1/2002 |
| EP | 1 264 547 A1 | 12/2002 |
| GB | 1379019 | 1/1975 |
| WO | WO 2007/033508 A2 | 3/2007 |

OTHER PUBLICATIONS

PCT/EP2010/054582—Written Opinion of the International Searching Authority, Jul. 16, 2010.
PCT/EP2010/054582—International Search Report, Jul. 16, 2010.
GB 09 06009.6 -Great Britain Search Report, Jun. 18, 2009.
Sun et al.; "Current Status and Prospects of Sulfur-containing Flavor Compounds in China"; Beijing Technology and Business University; Beijing, China; pp. 99-102; Dec. 31, 2006.
Xu, et al.; "Progress of Sulfur Spices"; Beijing Technology and Business University; Beijing, China; pp. 5-6; Feb. 28, 2006.
Search Report of the State Intellectual Property Office of the People's Republic of China; Application No. 201080015291.1; Mar. 5, 2013.

*Primary Examiner* — Leslie Wong
(74) *Attorney, Agent, or Firm* — Curatolo Sidoti Co., LPA; Joseph G. Curatolo; Salvatore A. Sidoti

(57) ABSTRACT

Provided are new O-alkyl S-hydroxyalkyl carbonothioates and O-alkyl S-alkoxyalkyl carbonothioates, their manufacture and their use as flavor and fragrance. Also provided are flavor and fragrance compositions comprising said substance, or a mixture thereof.

8 Claims, No Drawings

CARBONOTHIOATES AS FLAVOURS AND FRAGRANCES

CROSS REFERENCE TO RELATED APPLICATIONS

This application is a national stage application of International Application No. PCT/EP2010/054582, filed 7 Apr. 2010, which claims priority from Great Britain Patent Application Serial No. 0906009.6, filed 7 Apr. 2009, from which applications priority is claimed, and which are incorporated herein by reference.

Provided are new O-alkyl S-hydroxyalkyl carbonothioates and O-alkyl S-alkoxyalkyl carbonothioates, their manufacture and their use as flavour and fragrance. Also provided are flavour and fragrance compositions comprising one or more of said substances.

The flavour and fragrance industry is continuously interested in new ingredients that may enhance, improve or modify the flavour character of consumer products The flavour of edible products, such as foodstuffs and beverages consists of two parts: the aroma and the taste. In general, what is provided through the olfactory epithelium in the nasal cavity is referred to as "aroma", whereas the term "taste" is generally used to describe the sensory impact that is perceived via the mouth, especially the tongue.

Surprisingly, inventors have found that the flavour of edible products can be improved significantly by admixing thereto a O-alkyl S-hydroxyalkyl/alkoxyalkyl carbonothioate of formula (I) as hereinunder defined.

It has been found that the flavour of a product, compared with a product without a compound of formula (I) as hereinunder defined, was more intense and/or lasted longer. These properties were maintained under processing conditions, such as heating from about 75° C. to about 150° C., which make the compounds of formula (I) particularly suitable for processed foodstuff and beverages, such as instant coffee and powdered coffee beverages.

Accordingly, in a first embodiment, there is provided a compound of formula (I)

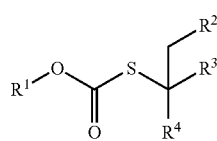

(I)

wherein
  $R^1$ is methyl, ethyl or n-propyl;
  $R^2$ is hydrogen or $C_1$-$C_4$ alkyl (e.g. $C_2$, or $C_3$ alkyl);
  $R^3$ is $C_2$, $C_3$ or $C_4$ hydroxyalkyl (e.g. hydroxylethyl, 1-hydroxyethyl, hydroxypropyl, hydroxyprop-2-yl, 1-methyl 2-hydroxypropyl, 2-hydroxypropyl), or $C_2$, $C_3$ or $C_4$ alkoxyalkyl (e.g. methoxyethyl, ethoxyl); and
  $R^4$ is hydrogen or methyl.

The compounds of formula (I) comprise several chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Non-limiting examples are compounds of formula (I) wherein $R^1$ is ethyl.

Further non-limiting examples are compounds of formula (I) wherein $R^1$ is ethyl and $R^4$ is hydrogen.

Further non-limiting examples are compounds of formula (I) wherein $R^1$ is methyl or ethyl, $R^3$ is $C_2$, $C_3$ or $C_4$ alkoxyalkyl (e.g. methoxyethyl), and $R^4$ is hydrogen.

In particular embodiments compounds of formula (I) are selected from
O-ethyl S-4-methoxy-2-methylbutan-2-yl carbonothioate
O-ethyl S-4-hydroxy-3-methylbutan-2-yl carbonothioate
O-ethyl S-4-hydroxy-3-methylpentan-2-yl carbonothioate
O-ethyl S-4-hydroxy-2-methylbutan-2-yl carbonothioate
O-ethyl S-4-hydroxy-2-methylpentan-2-yl carbonothioate
O-ethyl S-3-hydroxybutan-2-yl carbonothioate
O-ethyl S-1-hydroxyhexan-3-yl carbonothioate,
O-ethyl S-1-methoxyhexan-3-yl carbonothioate, and
O-methyl S-1-methoxyhexan-3-yl carbonothioate The compounds of formula (I) may be used alone or in combination with other substances useful for the required purpose, e.g. fragrances or flavours. Preferably however, the compounds of formula (I) may be combined with other flavours and/or fragrances selected from the extensive range of natural and synthetic molecules currently available, such as ethereal oils and extracts, alcohols, aldehydes and ketones, ethers and acetals, esters and lactones, macrocycles and heterocycles.

Accordingly, there is provided in a further embodiment a flavour composition comprising a compound of formula (I) and at least one further flavour ingredient.

In a further embodiment, the compounds of formula (I) may be admixed with one or more ingredients or excipients conventionally used in conjunction with flavours or fragrances in fragranced/flavoured applications, for example, carrier materials, and other auxiliary agents, such as solvents (e.g. dipropyleneglycol (DPG), isopropylmyristate (IPM), triethylcitrate (TEC), ethanol, propylene glycol (PG), triacetine, and benzylic alcohol, commonly used in the art. The compounds of formula (I) may be dissolved or dispersed in a carrier material, such as a fat, or enrobed with maltose-dextrin, gelatine, gum Arabic and the like. They may be mixed with the food ingredients ready to be prepared or mixed with one of the ingredients.

In a further embodiment there is provided a flavour application comprising a compound of formula (I) and a product base.

Flavoured applications for which the compounds of formula (I) are particularly suitable are foodstuffs and beverages such as dry, canned, frozen and instant soups, ready meals, croquettes, sauce cubes, bouillon cubes, baking fats, margarine, bread, cakes, and instant drinks which are prepared with hot water, such as instant coffee and powdered coffee beverages, beer, soft drinks, flavoured tea and dairy products. This list of products is given by way of illustration and is not to be regarded as being in any way limiting.

As used herein, by "product base" in conjunction with flavour applications is meant an edible product, not containing a compound of formula (I) as hereinabove defined.

As used herein, by "edible products" are meant products such as foodstuffs and beverages, or personal care products that are intended to be introduced into the oral cavity of a human or animal and remain there for a certain period of time before being ingested or removed from the mouth. Such products include compositions in their processed, partially processed or unprocessed state, The compound of formula (I) may be present in flavoured applications in amounts ranging from about 1 ppb ($10^9$; 1 μg/kg) to about 250 ppb ($10^9$; 250 μg/kg), more preferably from about 25 ppb to about 100 ppb, e.g. about 50 ppb.

If used in flavour compositions, the compound of formula (I) may be present in amounts ranging from about 0.005 g/kg to about 2 g/kg, more preferably from about 0.05 g/kg to about 1 g/kg, e.g. about 0.5 g/kg, based on the flavour composition.

In another embodiment, the compound of formula (I) may be used in a broad range of fragrance applications, e.g. in any field of fine and functional perfumery, such as perfumes, household products, laundry products, body care products and cosmetics.

If used in fragrance applications, the compound of formula (I) may be present in amounts ranging from about 1-30 ppm based on the fragrance application. However, these values are given only by way of example, since the experienced perfumer may also achieve effects or may create novel accord with lower or higher concentrations.

The compounds of formula (I) may be employed into a product base by mixing the compound, or a fragrance/flavour composition comprising it, with the product base, and/or they may, in an earlier step, be entrapped with an entrapment material, and then mixed with the consumer product base.

The compounds of formula (I) may be prepared as depicted in scheme 1 under conditions known to the skilled person. Further particulars as to reaction conditions are provided in the examples.

MTBE extraction were carried out. The resulting extracts were concentrated and distilled giving 51 g of the methylated intermediate in 62% yield.

Under nitrogen, 3-chloroperbenzoic acid (77%, 442 mmol) was added to a solution of (Z)-1-methoxyhex-3-ene (420 mmol) in 1.70 liter of dichloromethane at 10° C. After the addition was completed, the mixture was allowed to stir while warming up to room temperature. When the reaction was completed according to GC analyses, it was worked-up with sodium bicarbonate solution. The organic layer was concentrated and distilled giving 43 g of the oxirane intermediate in 79% yield.

Under nitrogen, cis-2-ethyl-3-(2-methoxyethyl)oxirane (323 mmol) was added dropwise to a solution of sulfuric acid (8.4 ml), thiourea (332 mmol) in 110 ml of DI water. The reaction mixture was allowed to stir to room temperature. When the reaction was completed according to GC analyses, its pH was adjusted to 10 with sodium carbonate and the resulting mixture was heated to 40° C. for an hour. The product mixture was extracted with MTBE and the resulting extracts were concentrated and distilled giving 29 g thiirane intermediate in 61% yield.

Under argon, a solution of 2-ethyl-3-(2-methoxyethyl)thiirane (34 mmol) in 5 ml of anhydrous THF was added dropwise to a mixture of LAH (17 mmol) in 40 ml of anhydrous THF. The mixture was refluxed and the reaction was monitored by GC. When the reduction was completed, it was worked-up according to the standard procedure. The product Scheme 1:

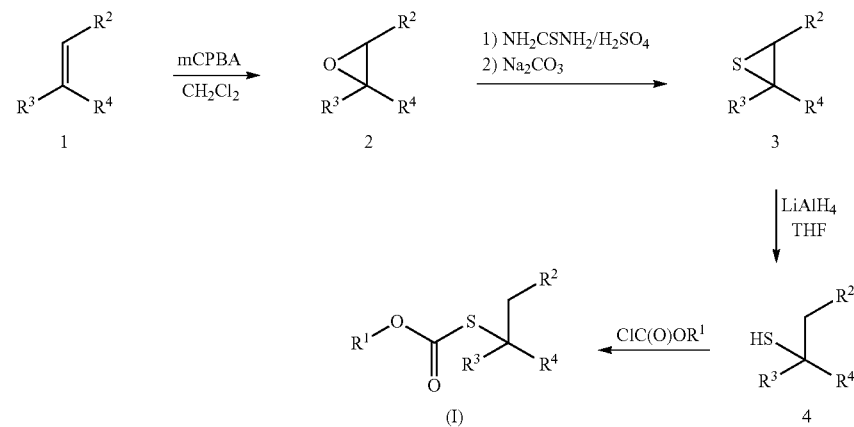

$R^1$, $R^2$, $R^3$, and $R^4$ have the same meaning as given for formula (I) above.

The invention is now further described with reference to the following non-limiting examples. These examples are for the purpose of illustration only and it is understood that variations and modifications can be made by one skilled in the art.

EXAMPLE 1

O-Ethyl S-1-methoxyhexan-3-yl carbonothioate

Under nitrogen, a solution of (Z)-3-hexenol (718 mmol) in 300 ml of anhydrous THF was added dropwise to sodium hydride (790 mmol) and iodomethane (823 mmol) in 800 ml of anhydrous THF at 22-29° C. When the reaction was completed according to GC analyses, an aqueous work-up and mixture was extracted with MTBE and the resulting extracts were concentrated giving 3.75 g of the thiol mixture.

The crude thiol and triethylamine (24 mmol) in 20 ml of hexane was added dropwise to a solution of ethyl chloroformate (48 mmol) in hexane (20 ml) in an ice bath. When the reaction was completed according to GC analyses, it was worked-up with acidic solution of HCl, and extracted with hexane. The extracts was concentrated and purified by a silica gel column giving 0.80 g of the product of formula (I) in 11% yield.

MS (EI): 45 (100), 71 (73), 55 (59), 115 (36), 83 (33), 82 (28), 29 (27), 147 (24), 118 (20), 41 (19), 85 (18), 59 (15), 114 (12), 67(12), 58 (10).

Flavour description: sulfury, blackcurrant, tropical, roasted coffee.

Odor description: mushroom, herbaceous, slightly cacao connation.

EXAMPLE 2

O-Methyl S-1-methoxyhexan-3-yl carbonothioate

Following the general procedure of Example 1 using methyl chloroformate instead of ethyl chloroformate 0.41 g of the title compound was prepared.

MS (EI): 45(100), 71 (61), 55 (56), 83(37), 115 (27), 59 (24), 82 (23), 41(19), 147(17), 104(16), 85 (15), 67 (11), 114 (10).

Flavour description: fresh dark roasted note.

Odor description: mushroom-onions, green, slightly fatty, fruity, mango like, passion fruit like, blackcurrant, and sulphur on top.

EXAMPLE 3

Regular Coffee

A regular coffee was prepared from the following ingredients:

| | |
|---|---|
| 50 g roasted coffee bean (50% Brazil, 50% Colombia) extracted with 350 ml of water | |
| Sugar | 50 g |
| Homogenized milk | 80 g |
| Skim milk powder | 9 g |
| Sodium bicarbonate | 0.6 g |
| Sugar esters | 0.8 g |
| Coffee Flavour | 0.5 g |
| Distilled water | ad 1000 g |

| Coffee Flavour | parts by weight 1/1000 |
|---|---|
| Tetramethyl Pyrazine | 1.0 |
| Furfuryl Mercaptan | 1.0 |
| Damascenone ((E)-1-(2,6,6-trimethylcyclohexa-1,3-dienyl)but-2-en-1-one) | 0.2 |
| 2-Methyl Pyrazine | 0.2 |
| Guaiacol (2-Methoxy Phenol) | 0.2 |
| 2-Acetyl Pyridine | 0.5 |
| 3-Ethyl Pyridine | 0.8 |
| Ethyl Cyclotene (3-ethyl-2-hydroxycyclopent-2-enone) @ 50% PG | 0.8 |
| Trimethyl Pyrazine | 2.0 |
| 3-Hydroxy-2-butanone | 6.0 |
| 2,3-Pentanedione | 8.0 |
| 3-Ethyl 2-Methyl Pyrazine | 3.0 |
| Para Vinyl Guaiacol (2-methoxy-4-vinylphenol) @ 10% PG | 6.0 |
| Triacetin | 970.3 |

To a portion of the regular coffee (coffee A) was added 0.1 ppm of O-ethyl S-1-methoxyhexan-3-yl carbonothoate, relative to the weight of the coffee (coffee B). The coffee was packed in cans and retorted at 123° C. for 20 minutes. By comparison the coffee containing a compound according to the invention (coffee B) exhibited an overall stronger coffee like impression, more body and rounded flavour profile.

EXAMPLE 4

Black Coffee

Black coffee was prepared from the following ingredients:

| | |
|---|---|
| 50 g roasted coffee bean (50% Brazil, 50% Colombia) extracted with 350 ml hot water | |
| Sodium bicarbonate | 0.3 g |
| Coffee Flavour (same as Example 3) | 0.5 g |
| Distilled water | ad 1000 g |

To a portion of the regular coffee (coffee C) was added 0.1 ppm of O-ethyl S-1-methoxyhexan-3-yl carbonothoate, relative to the weight of the coffee (coffee D). The coffee was packed in cans and retorted at 121° C. for 10 minutes. By comparison the coffee containing a compound according to the invention (coffee D) possessed an enhanced coffee roast and coffee bean like note. Furthermore it showed a greatly enhanced longlastiness compared to coffee C.

The invention claimed is:

1. A compound of formula (I)

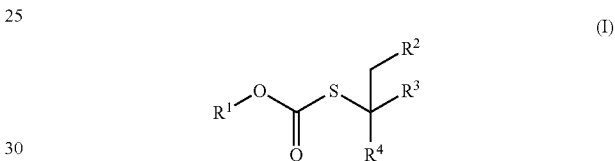

wherein
$R^1$ is methyl, ethyl or n-propyl;
$R^2$ is hydrogen or $C_1$-$C_4$ alkyl;
$R^3$ is $C_2$, $C_3$ or $C_4$ hydroxyalkyl, or $C_2$, $C_3$ or $C_4$ alkoxyalkyl; and
$R^4$ is hydrogen or methyl.

2. A compound according to claim 1 selected from the group consisting of
O-ethyl S-4-methoxy-2-methylbutan-2-yl carbonothioate
O-ethyl S-4-hydroxy-3-methylbutan-2-yl carbonothioate
O-ethyl S-4-hydroxy-3-methylpentan-2-yl carbonothioate
O-ethyl S-4-hydroxy-2-methylbutan-2-yl carbonothioate
O-ethyl S-4-hydroxy-2-methylpentan-2-yl carbonothioate
O-ethyl S-3-hydroxybutan-2-yl carbonothioate
O-ethyl S-1-hydroxyhexan-3-yl carbonothioate,
O-ethyl S-1-methoxyhexan-3-yl carbonothioate, and
O-methyl S-1-methoxyhexan-3-yl carbonothioate.

3. A flavour or fragrance composition comprising a compound of formula (I) as defined in claim 2 and at least one further flavour ingredient.

4. A flavour or fragrance application comprising a compound of formula (I) as defined in claim 1 and a product base.

5. A method of improving, enhancing or modifying a flavour or fragrance application comprising the step of adding thereto an olfactory acceptable amount of a compound of formula (I) as defined in claim 1.

6. A flavour or fragrance composition comprising a compound of formula (I) as defined in claim 1 and at least one further flavour ingredient.

7. A flavour or fragrance application comprising a compound of formula (I) as defined in claim 2 and a product base.

8. A method of improving, enhancing or modifying a flavour or fragrance application comprising the step of adding thereto an olfactory acceptable amount of a compound of formula (I) as defined in claim 2.

* * * * *